(12) United States Patent
Bercx et al.

(10) Patent No.: US 10,259,927 B2
(45) Date of Patent: Apr. 16, 2019

(54) POLYMER COMPOSITION HAVING LOW SENSORY IMPRESSION OF SMELL

(71) Applicant: SABIC GLOBAL TECHNOLOGIES B.V., Bergen op Zoom (NL)

(72) Inventors: Rick Robert Emilie Bercx, Geleen (NL); Hendrik Kormelink, Geleen (NL)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 124 days.

(21) Appl. No.: 15/129,737

(22) PCT Filed: Mar. 23, 2015

(86) PCT No.: PCT/EP2015/056131
§ 371 (c)(1),
(2) Date: Sep. 27, 2016

(87) PCT Pub. No.: WO2015/150146
PCT Pub. Date: Oct. 8, 2015

(65) Prior Publication Data
US 2017/0137597 A1    May 18, 2017

(30) Foreign Application Priority Data

Apr. 2, 2014   (EP) .................................... 14163186

(51) Int. Cl.
  *C08K 3/32*   (2006.01)
  *C08K 7/14*   (2006.01)
  *C08L 23/12*  (2006.01)
  *B60R 13/02*  (2006.01)
  *G01N 33/44*  (2006.01)
  *C08K 3/34*   (2006.01)
  *C08L 23/06*  (2006.01)
  *C08L 23/16*  (2006.01)

(52) U.S. Cl.
  CPC ................ *C08K 3/32* (2013.01); *B60R 13/02* (2013.01); *C08K 3/346* (2013.01); *C08K 7/14* (2013.01); *C08L 23/06* (2013.01); *C08L 23/12* (2013.01); *C08L 23/16* (2013.01); *G01N 33/442* (2013.01); *C08K 2003/325* (2013.01); *C08K 2201/007* (2013.01); *C08L 2205/025* (2013.01); *C08L 2205/035* (2013.01)

(58) Field of Classification Search
CPC ....................................................... C08K 3/32
See application file for complete search history.

(56) References Cited

U.S. PATENT DOCUMENTS

| | | | | |
|---|---|---|---|---|
| 3,980,611 | A | * | 9/1976 | Anderson ................ C08K 3/32 523/220 |
| 4,456,723 | A | * | 6/1984 | Breitenfellner .......... C08K 3/32 524/415 |
| 6,187,848 | B1 | | 2/2001 | Pixton et al. |
| 2008/0045638 | A1 | * | 2/2008 | Chapman ................ C08L 23/10 524/425 |
| 2012/0115995 | A1 | | 5/2012 | Lederer et al. |

FOREIGN PATENT DOCUMENTS

| | | |
|---|---|---|
| EP | 0611795 B2 | 8/1994 |
| WO | 2010149548 A1 | 12/2010 |
| WO | 2010149549 A1 | 12/2010 |

OTHER PUBLICATIONS

International Search Report; International Application No. PCT/EP2015/056131; International Filing Date Mar. 23, 2015; dated Jun. 9, 2015; 4 pages.
Written Opinion of the International Searching Authority; International Application No. PCT/EP2015/056131; International Filing Date Mar. 23, 2015; dated Jun. 9, 2015; 5 pages.

* cited by examiner

*Primary Examiner* — Michael F Pepitone
(74) *Attorney, Agent, or Firm* — Cantor Colburn LLP

(57) ABSTRACT

The present invention relates to a polymer composition having low sensory impression of smell comprising a polypropylene and a calcium salt of phosphoric acid, wherein in said polymer composition the amount of said calcium salt of phosphoric acid is preferably such to accomplish a sensory impression of smell measured according to VDA 270 of at most 4.0.

16 Claims, No Drawings

POLYMER COMPOSITION HAVING LOW SENSORY IMPRESSION OF SMELL

CROSS REFERENCE TO RELATED APPLICATIONS

This application is a 371 of International Application No. PCT/EP2015/056131, filed Mar. 23, 2015, which claims priority to European Application No. 14163186.1, filed Apr. 2, 2014 which are incorporated herein by reference in their entirety.

The present invention relates to a polymer composition having low sensory impression of smell (or low odor) and to an automotive article comprising such a polymer composition.

Polypropylene is the material of choice for many applications. For instance polypropylene in combination with mineral fillers, such as talc, is used in articles in the automotive interior. Said polypropylene/talc compositions are—generally speaking—good processable and can be individually customized. However such materials must also provide long term stability against environmental impacts, like oxidative degradation, keeping the tailored properties of the polypropylene/talc composition on the desired level. Accordingly antioxidants are added to impair the degradation of the polypropylene/talc compositions. It has been observed that such polypropylene compounds suffer from malodor.

International application WO2010149549 relates to an automotive interior article comprising phenolic antioxidants and the use of inosilicate in said article. According to this document the inosilicate resolves the problem of the automotive interior articles comprising heterophasic polypropylene (H-PPI), talc and phenolic antioxidants. The specific selection of inosilicate as a substitute of talc allows improving the sensory impression of smell as well as reducing the headspace emission of all volatiles, in particular of 2-methyl-I-propene, compared to standard automotive interior articles comprising talc and phenolic antioxidants.

International application WO2010149548 relates to a polypropylene mineral compound with reduced volatiles comprising phenolic antioxidants and the use of inosilicate in polymer compositions. The inosilicate is wollastonite, and the polymer composition comprises additionally phosphorous antioxidants.

EP 0611795 discloses a process for the manufacture of polypropylene resin expanded particles. The process comprises a step of dispersing polymer particles in water using calcium tertiary phosphate as a dispersant used for dispersing the polypropylene. EP 0611795 is not concerned with polymer compositions or articles manufactured therefrom having a low sensory impression of smell.

An object of the present invention is to provide a polymer composition having low odor.

Another object of the present invention is to provide a polymer composition having low odor while maintaining the mechanical properties on an acceptable level.

Another object of the present invention is to provide an automotive article manufactured on basis of a polymer composition having low odor.

The present invention thus relates to a polymer composition having low odor, comprising a polypropylene and a calcium salt of phosphoric acid. More in particular the present invention relates to a polymer composition having low odor, comprising polypropylene and from 0.1-1.0 wt % of a calcium salt of phosphoric acid, based on the weight of the polymer composition.

More preferably the present invention thus relates to a polymer composition having low odor, comprising a polypropylene and a calcium salt of phosphoric acid, wherein in said polymer composition the amount of said calcium salt of phosphoric acid is such to accomplish a sensory impression of smell measured according to VDA 270 to below 4.0

On basis of the presence of a calcium salt of phosphoric acid in a polypropylene composition one or more of the afore mentioned objects can be achieved. VDA 270 is a standard for a determining the odor of automotive articles, issued by Verband der Automobilinindustrie e.V. The determination takes places under supervision of a panel of at least three different people and the odor is classified in several classifications, i.e. from #1 (not perceptible) to #6 (intolerable). The measurement applied here is VDA 270, October 1992. The outcome of the determination is reported with one digit accuracy using half steps, such as for example 3.0, 3.5 or 4.0. This number represents the average of the classifications by the members of the testing panel.

Preferred embodiments of the calcium salt of phosphoric acid are chosen from the group of tricalcium phosphate ($Ca_3(PO_4)_2$), calcium pyrophosphate ($Ca_2P_2O_7$), dicalcium phosphate ($CaHPO_4$) and monocalcium phosphate ($Ca(H_2PO_4)_2$). Tricalcium phosphate $Ca_3(PO_4)_2$ is preferred. Tricalcium phosphate is also known as calcium hydroxide phosphate, calcium orthophosphate, calcium phosphate tribasic, penta-calcium hydroxide triphosphate, tert-calcium phosphate or tri-calcium di-orthophosphate. Please note some compounds mentioned before can also be described in its hydrated version, such as $CaHPO_4.2H_2O$. Preferably the sensory impression of smell measured according to VDA 270 is at most 3.5 more preferably at most 3.0. The lower limit of the sensory impression of smell measured according to VDA 270 is 1, indicated as "not perceptible".

The amount of calcium salt of phosphoric acid in the present polymer composition is preferably in the range of 0.1-1.0 wt %, such as in the range 0.2 wt. %-0.75 wt. %, more preferably 0.25 wt. %-0.6 wt. %, based on the total weight of said polymer composition.

The present polymer composition may further comprise additional components, such as ethylene alpha-olefin copolymers, for example C2-C3 copolymers, elastomers, mineral fillers, impact modifier and reinforcement agents. Other additional components or additives in this field antioxidants, antiozonants, antistatic agents, biocides, antimicrobials, antibacterial agents, blowing/foaming agents, carbon black, flame retardants, smoke suppressants, impact modifiers, light stabilizers, such as compounds of the class HALS, UV absorbers, pigments, colorants and plasticizers.

According to an embodiment of the present invention, the present polymer composition comprises 10-99.9 wt. % of a polypropylene, chosen from the group of a homopolymer and impact copolymer, 0-40 wt. % of a C2-C3 copolymer, 0-20 wt. % of an elastomer, 0-50 wt. % of a mineral filler and or reinforcement agent, and 0.25 wt. %-0.75 wt. %, of a calcium salt of phosphoric acid, wherein preferably the amount of talc as mineral filler is in a range of 1-30 wt. %, all percentages based on the total weight of said polymer composition.

According to a preferred embodiment the present polymer composition comprises 10-90 wt % of one or more polypropylenes, 5-20 wt % of an elastomer, 5-30 wt % of talc and 0.1-1 wt % of a calcium salt of phosphoric acid, the weight percentages based on the total weight of the composition.

According to a preferred embodiment the present polymer composition is a long-glass fibre reinforced polypropylene (LGF-PP) composition comprising glass fibres, wherein the long-glass fibre reinforced polypropylene is of the type wire-coated LGF-PP or pultrusion-grade LGF-PP.

Long glass fibre-reinforced compositions are generally prepared by a sheathing or wire-coating process, by cross-head extrusion or several pultrusion techniques. Using these technologies, impregnated or coated fibre strands are formed; these may then be cut into lengths, the pellets or granules thus obtained being suitable for further processing, i.e. for injection moulding and compression moulding as well as for extrusion compression moulding processes, into (semi)-finished articles. Long glass fibre-reinforced polymer compositions contain glass fibres having a length of at least 1 mm, often at least 2 mm and typically between 5 and 20 mm. As a result, glass fibres in moulded articles made from long glass fibre-reinforced polymer compositions generally are of higher length than in articles made from short glass fibre compositions, resulting in better mechanical properties.

In a pultrusion process, a bundle of continuous glass filaments is spread out into individual filaments and drawn through an impregnation die, into which the molten thermoplastic is injected, aiming at entirely wetting and impregnating each filament with the molten thermoplastic. Finally the strand is chopped into segments of the desired length. The glass fibres are generally parallel to one another in the segment, with each fibre being individually surrounded by the thermoplastic.

The process of sheathing or wire-coating is done without wetting the fibres individually with thermoplastic, but by forming a continuous outer sheath of a thermoplastic material around the continuous multifilament strand surface. The sheathed continuous strand is cut into pellets or granules of desired length, e.g. for about 12 mm length, in which the fibres are generally parallel to one another and have the same length as the pellets or granules. The pellets are further supplied to an injection moulding or compression moulding machine, and during this moulding step the glass fibres are dispersed within the thermoplastic polymer and formed into moulded (semi)-finished articles. In order to facilitate a proper dispersion of the glass fibres, the continuous strand can be treated with a coating or impregnating composition before applying a sheath of thermoplastic polymer.

The thermoplastic polymer used in the sheathing process is a crystalline polypropylene, like a propylene homopolymer, a random copolymer, or a so-called heterophasic copolymer of propylene and ethylene and/or another alpha-olefin. As mentioned before, the thermoplastic polymer may further contain one or more of usual additives, like stabilizers, processing aids, impact-modifiers, flame-retardants, acid scavengers, inorganic fillers, colorants, or components that further enhance properties of the reinforced compound, like compounds that enhance interfacial bonding between polymer and glass filaments. An example of the last compounds is a functionalized polyolefin, like a maleated polypropylene, in case the thermoplastic is a polypropylene.

The present invention further relates to the use of a calcium salt of phosphoric acid in a polymer composition comprising polypropylene to accomplish a sensory impression of smell measured according to VDA 270 to at most 4.0.

According to an embodiment of the present use the calcium salt of phosphoric acid is preferably chosen from the group of tricalcium phosphate ($Ca_3(PO_4)_2$), calcium pyrophosphate ($Ca_2P_2O_7$), dicalcium phosphate ($CaHPO_4$) and monocalcium phosphate ($Ca(H_2PO_4)_2$), preferably tricalcium phosphate $Ca_3(PO_4)_2$. Please note some compounds mentioned before can also be described in its hydrated version, such as $CaHPO_4.2H_2O$.

According to another embodiment of the present use the calcium salt of phosphoric acid is preferably present in an amount of 0.25 wt. %-0.75 wt. %, preferably 0.1 wt. %-0.6 wt. %, based on the total weight of said polymer composition.

In addition, the present invention relates to an automotive interior article comprising the present polymer composition.

The present invention generally relates to articles prepared by injection moulding or compression moulding of the composition according to the invention. Preferably these articles are non-expanded, i.e. the articles are not foamed. To that extent the composition of the present invention does not contain a physical or chemical foaming agent.

Preferred automotive interior articles comprising the present polymer composition are chosen from the group of dashboards, dashboard carriers, door claddings, door fixtures, armrests, pillar cladding, seat cladding, boot cladding and interior trims, parts used in heating, ventilation and/or air conditioning instruments.

Bumpers, cladding, and exterior trim may also be manufactured from the present polypropylene composition.

The invention will be further elucidated with reference to the following non-limiting experiments.

EXPERIMENTS

Different polypropylene compositions were prepared according to the list of components mentioned in Table 1 and Table 2. The compositions of Table 1 are based on SABIC PP 612 propylene copolymer. To an amount of about 65 wt % of polypropylene was added a polyethylene (6 wt %) and an ethylene elastomer (8 wt %) so as to form a total amount of 14 wt %. The additives are comprised of antioxidants and stabilisers common in the art. The variations in amount of TCP-SF (calcium phosphate) were corrected by the amount of polypropylene. All amounts are in weight % based on the weight of the polymer composition. The VDA 270 C3 note is the sensory impression of smell. Individual notes of the test panel are also provided herein.

TABLE 1

|  | Ref. (1) | Ref. (2) | E1 | E2 | E2 | E3 | E4 | E5 | E6 |
|---|---|---|---|---|---|---|---|---|---|
| TCP-SF | 0 | 0 | 0.1 | 0.2 | 0.5 | 0.5 | 0.75 | 1 | 2 |
| SABIC PP 612 | 65.05 | 65.05 | 64.95 | 64.85 | 64.55 | 64.55 | 64.30 | 64.05 | 63.05 |
| PE and Rubbers | 14 | 14 | 14 | 14 | 14 | 14 | 14 | 14 | 14 |
| Talc | 20 | 20 | 20 | 20 | 20 | 20 | 20 | 20 | 20 |
| Additives | 0.95 | 0.95 | 0.95 | 0.95 | 0.95 | 0.95 | 0.95 | 0.95 | 0.95 |
| VDA270 C3 note | 4 | 4 | 4 | 3.5 | 3 | 3.5 | 3.5 | 3.5 | 4 |
| VDA270 C3 | 4.0 | 4.0 | 4.0 | 3.0 | 3.5 | 3.5 | 3.5 | 3.5 | 4.0 |
| individual | 4.5 | 4.0 | 4.5 | 4.0 | 3.0 | 3.5 | 3.5 | 3.5 | 4.0 |
| notes | 4.0 | 4.0 | 4.5 | 4.0 | 3.0 | 3.5 | 3.5 | 3.5 | 4.0 |

TABLE 1-continued

|  | Ref. (1) | Ref. (2) | E1 | E2 | E2 | E3 | E4 | E5 | E6 |
|---|---|---|---|---|---|---|---|---|---|
|  | 3.5 | 4.0 | 3.5 | 3.5 | 3.0 | 3.5 | 4.0 | 4.0 | 4.0 |
|  | 4.0 | 4.5 | 4.0 | 3.5 | 3.5 | 3.5 | 4.0 | 4.0 | 4.0 |
| VDA 270 C3 average | 4.0 | 4.1 | 4.1 | 3.6 | 3.2 | 3.5 | 3.7 | 3.7 | 4.0 |

Table 2 shows similar experiments based on SABIC PP 513 propylene copolymer in a compound of a somewhat more complex composition. Again the weight of TCP-SF is corrected only via the amount of polypropylene (PP513). All amounts are in weight % based on the weight of the polymer composition.

TABLE 2

|  | Ref. | E7 | E8 | E9 | E10 | E11 | E12 |
|---|---|---|---|---|---|---|---|
| TCP-SF | 0 | 0.1 | 0.2 | 0.5 | 0.75 | 1 | 2 |
| SABIC PP 513 | 46.85 | 46.75 | 46.65 | 46.35 | 46.1 | 45.85 | 44.85 |
| SABIC PP 612 | 15 | 15 | 15 | 15 | 15 | 15 | 15 |
| SABIC PP 95610 | 10 | 10 | 10 | 10 | 10 | 10 | 10 |
| PE and Rubbers | 16 | 16 | 16 | 16 | 16 | 16 | 16 |
| talc | 10 | 10 | 10 | 10 | 10 | 10 | 10 |
| Additives | 2.15 | 2.15 | 2.15 | 2.15 | 2.15 | 2.15 | 2.15 |
| VDA270 C3 note | 4 | 3.5 | 3.5 | 3 | 4.5 | 4 | 4 |
| VDA270 C3 individual notes | 4.0 | 3.5 | 3.0 | 3.0 | 4.0 | 4.0 | 4.0 |
|  | 4.5 | 3.5 | 3.0 | 3.0 | 4.5 | 4.0 | 4.0 |
|  | 4.0 | 4.0 | 3.5 | 3.0 | 4.5 | 4.5 | 4.0 |
|  | 4.0 | 3.0 | 3.5 | 3.5 | 5.0 | 4.0 | 3.5 |
|  | 4.0 | 3.0 | 3.5 | 3.0 | 5.0 | 4.0 | 4.0 |
| VDA 270 C3 average | 4.1 | 3.4 | 3.3 | 3.1 | 4.6 | 4.1 | 3.9 |

This table 2 shows that example E10 has a relatively high VDA 270 C3 note. The present inventors believe that this value is an outlier, the exact cause for which could not be established.

The calcium salt of phosphoric acid used in all Examples is tricalcium phosphate TCP SF, supplied by Budenheim. The sensory impression of smell (odor) is provided based on determination according to VDA 270 C3 (1992) meaning that the sample size (Probekörpermenge) is according to variant C, meaning 50+/−5 cm$^3$ (for a 1 liter vessel) or 150+/−15 cm$^3$ (for a 3 liter vessel) and wherein the test is carried out according to variant 3, meaning at a temperature of 80+/−2° C. for a time (Lagerdauer) of 2 h+/−10 min. A test panel of five people was used, the individual notes have been provided. The VDA 270 C3 note is expressed in half points, following the requirements of this standard. For the purpose of analysis a numerical average has been provided also, such not being strictly conform the standard.

The experimental data supports the finding that the smell (odor) of a polypropylene composition is improved by addition of a calcium salt of phosphoric acid.

The invention claimed is:

1. Polymer composition having low sensory impression of smell comprising a polypropylene, 1-30 wt % of talc, and from 0.2-0.6 wt % of a calcium salt of phosphoric acid, weight percentages based on the weight of the polymer composition, wherein the low sensory impression of smell is at most 4.0 according to VDA 270 (1992).

2. Polymer composition according to claim 1, wherein said calcium salt of phosphoric acid is chosen from the group of tricalcium phosphate ($Ca_3(PO_4)_2$), calcium pyrophosphate ($Ca_2P_2O_7$), dicalcium phosphate ($CaHPO_4$) and monocalcium phosphate ($Ca(H_2PO_4)_2$).

3. Polymer composition according to claim 1, further comprising any one or more of C2-C3 copolymers, elastomers, impact modifier and reinforcement agents.

4. Polymer composition according to claim 1, comprising wt. % of a polypropylene, selected from the group of a propylene homopolymer and propylene impact copolymer, 0-40 wt. % of a C2-C3 copolymer, 0-20 wt. % of an elastomer, 0-50 wt. % of a reinforcement agent, 1-30 wt % of talc, and 0.2-0.6 wt. % of said metal salt of phosphoric acid, all percentages based on the total weight of said polymer composition.

5. Polymer composition according to claim 1, wherein said calcium salt of phosphoric acid is present in an amount of 0.25 wt. %-0.6 wt. %, based on the total weight of said polymer composition.

6. Polymer composition according to claim 1, wherein said polymer composition is a long-glass fibre reinforced polypropylene (LGF-PP) composition comprising glass fibres.

7. Polymer composition according to claim 6, wherein said long-glass fibre reinforced polypropylene is of the type wire-coated LGF-PP or pultrusion-grade LGF-PP.

8. A method for attaining a sensory impression of smell measured according to VDA 270 of at most 4.0, comprising adding 0.2-0.6 wt % of a calcium salt of phosphoric acid to a polymer composition comprising polypropylene and 1-30 wt % of talc, based on the weight of the polymer composition, to accomplish the sensory impression of smell measured according to VDA 270 of at most 4.0.

9. The method according to claim 8, wherein said calcium salt of phosphoric acid is chosen from the group of tricalcium phosphate ($Ca_3(PO_4)_2$), calcium pyrophosphate ($Ca_2P_2O_7$), dicalcium phosphate ($CaHPO_4$) and monocalcium phosphate ($Ca(H_2PO_4)_2$).

10. The method according to claim 8, wherein said calcium salt of phosphoric acid is present in an amount of 0.25 wt. % to 0.6 wt. %, based on the total weight of said polymer composition.

11. Automotive interior article comprising a polymer composition according to claim 1.

12. Automotive interior article according to claim 11, wherein said article is chosen from the group of dashboards, dashboard carriers, door claddings, door fixtures, armrests, pillar cladding, seat cladding, boot cladding interior trims and parts used in heating, ventilation and/or air conditioning instruments.

13. Polymer composition according claim 1, wherein said calcium salt of phosphoric acid comprises tricalcium phosphate $Ca_3(PO_4)_2$, further comprising any one or more of C2-C3 copolymers, elastomers, impact modifier and reinforcement agents.

14. Polymer composition according to claim 13, wherein said polymer composition is a long-glass fibre reinforced polypropylene (LGF-PP) composition comprising glass fibres.

15. Polymer composition according to claim 14, wherein said long-glass fibre reinforced polypropylene is of the type wire-coated LGF-PP or pultrusion-grade LGF-PP.

16. Polymer composition according to claim 13, wherein said calcium salt of phosphoric acid is present in an amount of 0.25 wt. %-0.6 wt. %, based on the total weight of said polymer composition.

\* \* \* \* \*